(12) United States Patent
Nyholm et al.

(10) Patent No.: US 9,305,395 B2
(45) Date of Patent: *Apr. 5, 2016

(54) DENTAL IMAGING APPARATUS

(75) Inventors: Kustaa Nyholm, Siuntio (FI); Christian De Godzinsky, Vantaa (FI); Juha Koivisto, Helsinki (FI)

(73) Assignee: PLANMECA OY, Helsinki (FI)

( * ) Notice: Subject to any disclaimer, the term of this patent is extended or adjusted under 35 U.S.C. 154(b) by 530 days.

This patent is subject to a terminal disclaimer.

(21) Appl. No.: 13/576,178

(22) PCT Filed: Feb. 2, 2011

(86) PCT No.: PCT/FI2011/050090
§ 371 (c)(1),
(2), (4) Date: Jul. 31, 2012

(87) PCT Pub. No.: WO2011/095694
PCT Pub. Date: Aug. 11, 2011

(65) Prior Publication Data
US 2012/0300895 A1    Nov. 29, 2012

(30) Foreign Application Priority Data

Feb. 2, 2010 (FI) ...................... 20100036
Feb. 2, 2010 (FI) ...................... 20100037

(51) Int. Cl.
A61B 6/00 (2006.01)
G06T 17/00 (2006.01)
A61B 5/00 (2006.01)
A61B 5/107 (2006.01)
A61B 6/03 (2006.01)
A61B 6/14 (2006.01)

(52) U.S. Cl.
CPC ............... *G06T 17/00* (2013.01); *A61B 5/0064* (2013.01); *A61B 5/1079* (2013.01); *A61B 6/032* (2013.01); *A61B 6/14* (2013.01); *A61B 6/4417* (2013.01); *A61B 6/5247* (2013.01)

(58) Field of Classification Search
USPC .............................................. 378/4
See application file for complete search history.

(56) References Cited

U.S. PATENT DOCUMENTS

| 5,278,756 | A | * | 1/1994 | Lemchen et al. ............. 600/587 |
| 6,081,739 | A | * | 6/2000 | Lemchen ............. A61B 5/0064 |
| | | | | 600/407 |
| 2002/0176612 | A1 | | 11/2002 | Tuncay et al. |
| 2004/0254456 | A1 | | 12/2004 | Ritter |
| 2004/0258210 | A1 | | 12/2004 | Ritter |
| 2007/0262983 | A1 | | 11/2007 | Choi |
| 2008/0056439 | A1 | | 3/2008 | Thompson et al. |

FOREIGN PATENT DOCUMENTS

| DE | 10317137 A1 | 11/2004 |
| DE | 10315242 B4 | 2/2006 |

(Continued)

*Primary Examiner* — Phillip A Johnston
(74) *Attorney, Agent, or Firm* — Fay Sharpe LLP

(57) ABSTRACT

The invention relates to a dental imaging apparatus which includes an x-ray imaging means and at least one color camera for photographing the face of a patient positioned at the imaging station of the apparatus, which at least one color camera is arranged to image the patient's face positioned at the patient support station from different directions, and means arranged into functional connection with said at least one color camera for creating a virtual three-dimensional texture model of the patient's face.

26 Claims, 5 Drawing Sheets

(56) References Cited

FOREIGN PATENT DOCUMENTS

| EP | 2 130 491 A1 | 12/2009 |
| JP | 2006-204330 | 8/2006 |
| WO | WO 2009/140582 | 11/2000 |
| WO | WO 2004/098378 | 11/2004 |
| WO | WO 2006/071002 | 7/2006 |
| WO | WO 2008/019355 | 2/2008 |
| WO | WO 2008/072398 | 6/2008 |

* cited by examiner

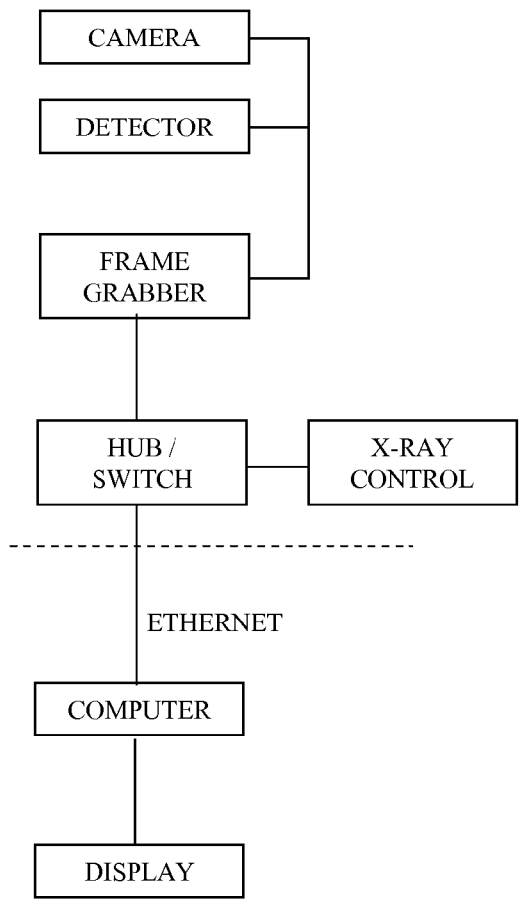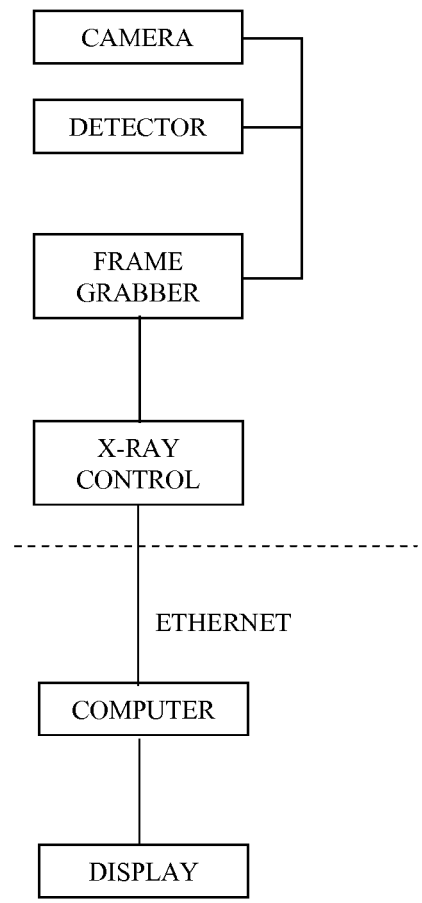
Fig. 4a                    Fig. 4b

DENTAL IMAGING APPARATUS

FIELD OF INVENTION

The invention relates to a dental imaging apparatus according to the preamble of claim 1.

BACKGROUND OF INVENTION

The history of medical x-ray imaging originates approximately to the time of inventing x-radiation. For more advanced ways of imaging, e.g. the development of panoramic x-ray imaging in the dental field started for over a half century ago. The development of digital imaging especially in the 1990s brought digital x-ray imaging devices also to dental practices. The latest development step in the dental field has been the generalisation of the cone-beam computed tomography apparatus designed for three-dimensional imaging of skeletal structures of the cranial area. Concerning new possibilities offered by them, worth mentioning is e.g. applications related to implant attachment and other treatment planning.

Along with the development of cameras and information technology, such as that of computing power of computers, it has become possible to create virtual three-dimensional surface models of different surfaces. In the dental field, facial surface models can be utilised e.g. in connection with orthodontic treatment, as orthodontic treatment can also have an effect on facial shapes. Such surface models have sometimes been combined with information on surface texture, i.e. that of details of the surface/surface structure.

The prior art also includes techniques to create a virtual three-dimensional texture model without a separately created model of the three-dimensional shape of the surface.

Among others, the need for acquiring a separate device for a particular imaging purpose has been limiting utilisation of facial texture models in the dental field. Acquiring a separate device is not only a question of costs but also of space, as each device always requires a space to be installed and/or stored in and/or where it can be used. On the other hand, each separate imaging always takes a certain amount of time, too. Furthermore, as far as data processing is concerned, there are certain challenges in the arrangements in which creating the model requires combining image information acquired at different times, image information acquired by different imaging devices and/or image information acquired of an anatomy having been positioned in different ways for imaging.

BRIEF DESCRIPTION OF INVENTION

The object of the invention is a versatile dental imaging apparatus, by means of which it is possible to create for the virtual three-dimensional modelling of a patient's skull at least x-ray image information on the patient's cranial skeletal structure and, further, information on the colours, scars, hair, moles etc. of the patient's face. The apparatus according to the invention includes means for producing not only x-ray images but also three-dimensional images comprising a facial surface texture. Preferably, the apparatus is arranged to enable creating 3D images on the cranial skeletal structure and/or teeth and, with the same patient positioning and imaging event, information on facial soft-tissue surface shapes and surface texture. Essential characteristics of the invention are defined in more detail in the accompanying patent claims.

The invention introduces a new arrangement for versatile modelling of the patient's cranial anatomy. The invention enables, among others, using existing imaging devices and avoiding the need to use prior-art special arrangements, which lowers the dentists' threshold to employ the possibilities offered by virtual 3D models.

Next, the invention and its preferable embodiments will be described in more detail also with reference to the enclosed figures.

BRIEF DESCRIPTION OF FIGURES

FIGS. 4a and 4b show signal paths according to one preferable embodiment of the invention from an x-ray detector and at least one colour camera via a frame grabber to a computer.

DETAILED DESCRIPTION OF INVENTION

Figure 1:
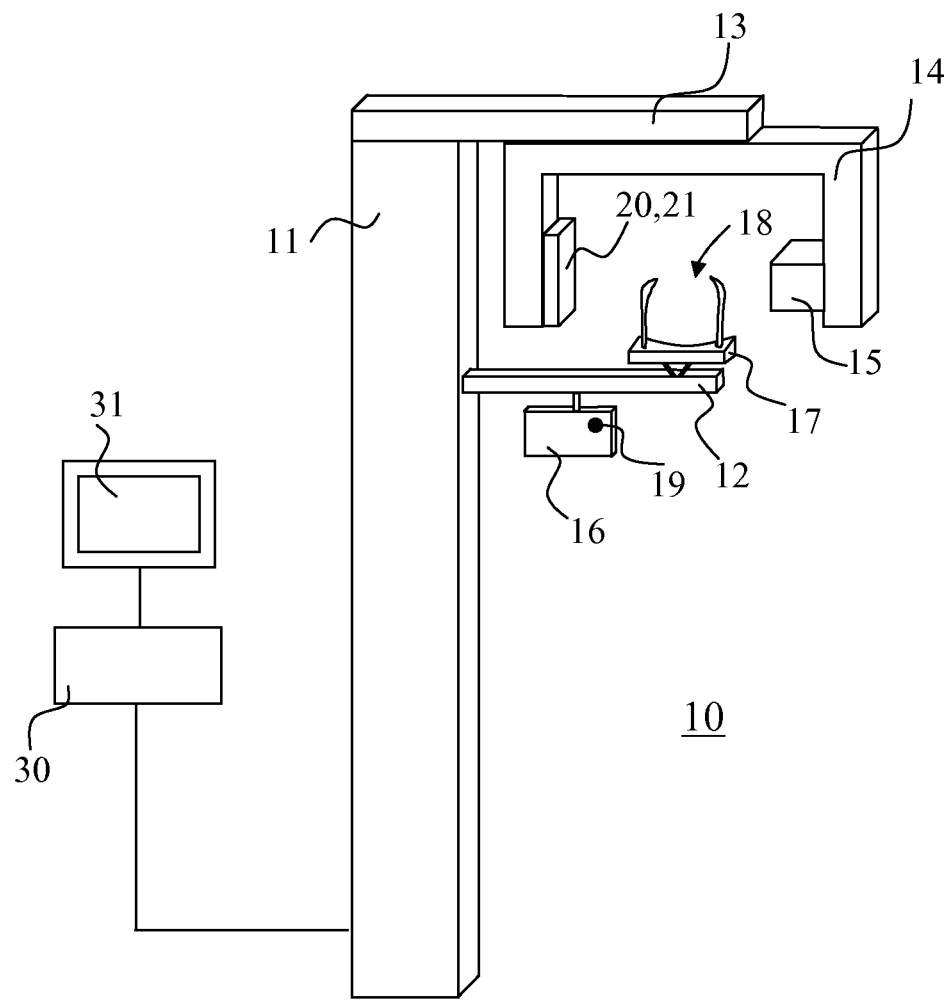
FIG. 1 shows one imaging apparatus according to the invention, the basic structure of which includes a base construction and an arm part supporting imaging means.

FIG. 1 shows one imaging apparatus according to the invention. The apparatus includes a vertical support construction (11) from which horizontally extends an arm (12) supporting a patient support means and an arm part (13) which supports a structure supporting imaging means of the apparatus, an arm part (14). The arm part supporting the imaging means (14) may be arranged rotatable. To the arm part supporting the imaging means (14) are arranged at a distance from each other an x-ray source (15) and a receiver of x-ray image information (21), which are located at the apparatus with respect to a patient support means (17) such that an imaging station (18) is created to the apparatus which is located between the x-ray source (15) and the receiver means of x-ray image information (21) such that a beam produced by the x-ray source (15) can be directed to go through said imaging station (18) towards the receiver means of x-ray image information (21). The apparatus includes control means, of which FIG. 1 shows a control panel (16) arranged to the support construction (11) and operating mode selection means (19) pertaining in it. In the apparatus according to FIG. 1, the receiver means of x-ray image information (21) are arranged as part of a receiver module of image information (20) which is arranged into connection with a computer (30) via a cable. A means for processing image information is arranged to the computer, and a display (31) to present images created by the computer.

Figure 2:
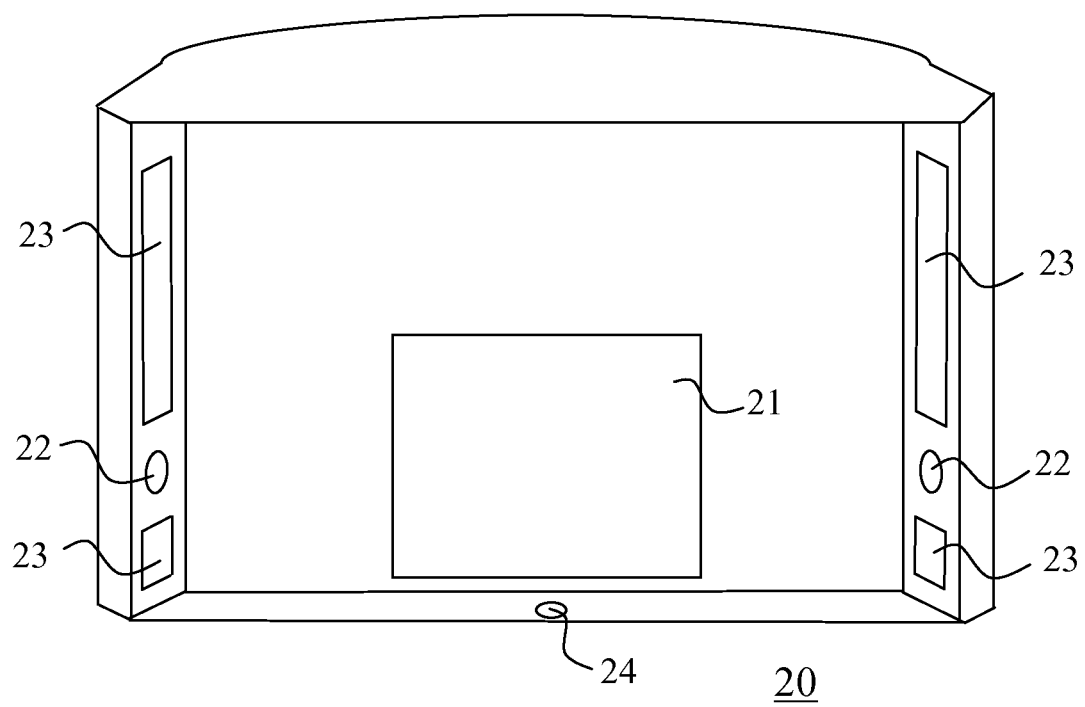
FIG. 2 shows a receiver module of image information applicable for use in the apparatus according to FIG. 1.
Figure 3:
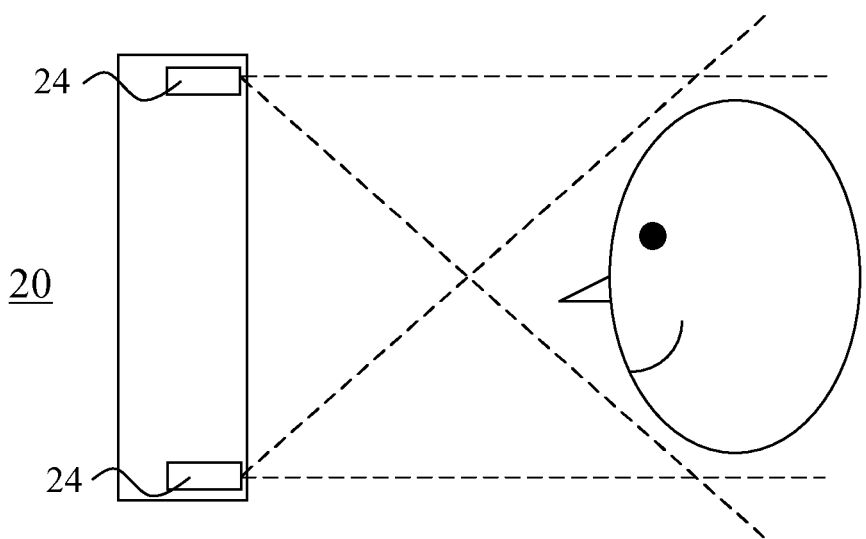
FIG. 3 shows directing of laser beams from the module according to FIG. 2 towards a patient positioned at an imaging station.

FIG. 2 shows a receiver module of image information (20) applicable for use in the apparatus according to FIG. 1. The module includes two colour cameras (22) arranged horizontally on opposite sides of the x-ray detector (21) and aligned at the imaging station (18). Further, light sources (23) preferably producing white light to illuminate the imaging station (18) and two lasers (24) are arranged to the module (20). These lasers are positioned substantially in the middle of the module (20) to the substantial proximity of its upper and lower edges. The lasers (24) are arranged to emit and direct at the imaging station (18) a narrow vertical planar fan beam which casts a laser light pattern on the patient's face. FIG. 3 shows how the laser fan beams produced by the two lasers

(24) shown in FIG. 2 can be directed at the imaging station (18) to cover the patient's face in the vertical direction without shadow areas.

The invention can employ two lasers (24) of the same colour or they may be of different colour, the first can be arranged to produce laser light of a first and the other of a second colour. When using lasers of the same colour, it can be challenging to implement the structure in practice such that the lasers (24) produce exactly overlapping beams. This can already be difficult from the viewpoint of manufacturing techniques and, further, alignment problems may also occur later on when using the device. As regards to lasers of different colours, they can be arranged to point at different directions and can be identified in the image e.g. by machine vision based on searching the image for the hues in question. If the mutual alignment of the lasers of different colours changes during use, instead of realigning the lasers (which could require service at the factory), it is possible to fix the situation by recalibration.

The light sources (23) arranged to the apparatus can be arranged to produce lights of other colour or colours than white, too. Diffusing foils may be arranged in front of the light sources (23) (cf. surface (23) in FIG. 2), whereby light is emitted from a larger area and substantially evenly and illumination in the target area will be even. Furthermore, the light sources (23) may be provided with polarizers (cf. surface (23) in FIG. 2) which can eliminate mirror reflection from the skin surface possibly otherwise visible in the image of the second camera, caused by the light source located in connection with the first camera, and vice versa. It is also possible to arrange to the apparatus more than two or only one colour camera (22), and the cameras or camera (22) can be arranged to operate not only as a photographic camera but also as a continuously-operating video camera. The light pattern to be directed on the patient's face can be produced by some other light source than a laser and the colour of this light pattern, too, can be arranged changeable and, even when produced by a laser, its colour can be some other than the conventional red, such as preferably particularly green.

When the structure supporting the imaging means (14) of the apparatus according to FIG. 1 is arranged rotatable, it is possible for the one or more colour cameras (22) arranged to the receiver module of image information (20) to shoot images from the patient's face positioned at the imaging station (18) from different directions. Then, it is also possible to make the laser light pattern to scan the patient's face. When using e.g. the arrangement according to FIG. 2, in which the camera (22) and the laser (24) are positioned at a distance from each other, it is possible to scan the patient's face positioned at the imaging station (18) with the laser line and, at the same time, to shoot images of the face at an angle (at an angle of less than 90 degrees) with respect to the direction of the laser beam. Of the image information acquired this way, it is possible to produce a three-dimensional surface model of the patient's facial shape. In one preferable embodiment of the invention, the control system of the apparatus is provided with a control function to always momentarily switch off the laser for a desired duration during a scan, during which periods it is possible to shoot colour images of the patient's face without the laser light pattern and to produce from the hence acquired image information a texture model of the patient's face. However, it is in principle possible to operate also such that the laser is not switched off at all but the laser line is removed from the texture model being formed during processing of the image information produced in the imaging programmatically.

FIG. 4a shows a signal path from the receiver module of image information (20) to the computer (30) used in one preferable embodiment of the invention. The signal path of image information detected by the colour camera or cameras (22) and the x-ray detector (21) to the computer (30) can be arranged shared such that the image information acquired from them is directed to the computer (30) via the same one frame grabber. Preferably, a signal path is also arranged in the apparatus at least between the control means of the movements of the imaging means and/or the control means of the x-ray source and the computer via the same Ethernet cable as the signal path from the camera to the computer. This can be implemented e.g. by means of an Ethernet-HUB component or an Ethernet switch component arrangeable to the apparatus. FIG. 4b shows another preferable embodiment for arranging signal paths to the apparatus which also requires only one Ethernet cable between the imaging means and the computer.

The means arranged to the computer (30) to process image information acquired when imaging the patient's face arranged at the imaging station (18) comprise, according to the invention, an algorithm for processing at least image information acquired from the x-ray detector (21) and for processing image information acquired from the colour camera or cameras (22) to create a virtual three-dimensional texture model of the patient's face. The texture model can be produced either solely of the photography information picturing the patient's face from more than one direction, or its production can utilise e.g. information on the shape of the surface of the soft-tissue of the patient's face acquired when x-ray imaging the patient. In a preferable embodiment of the invention, the image processing means includes a means for creating a facial surface model from the image information of the laser line directed on the patient's face, which information can be utilised in producing the three-dimensional texture model of the patient's face. Preferably, the image processing means includes a means which can produce models which simultaneously show three-dimensionally both the facial texture and at least parts of the teeth and/or skeletal structure of the patient's cranial area.

Figure 5A:
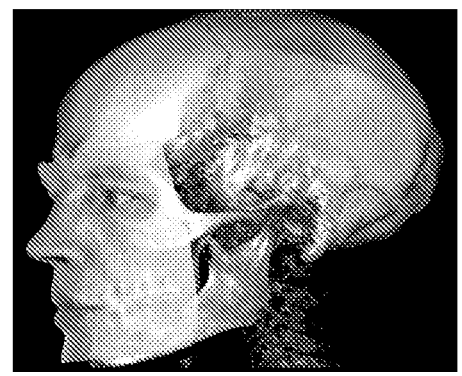
FIGS. 5a-5c show examples on various virtual three-dimensional facial models.
Figure 5B:
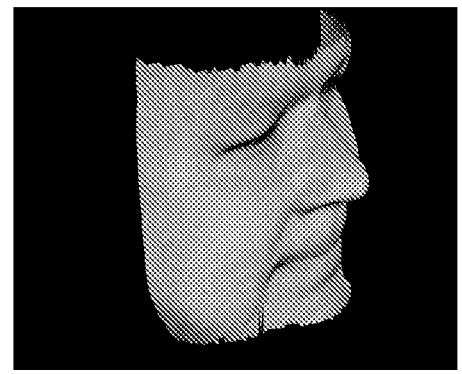
Figure 5C:
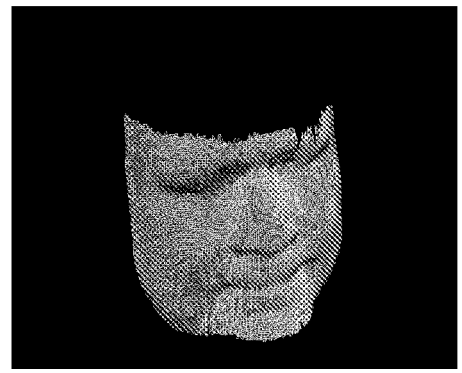

FIG. 5a shows an example of a facial three-dimensional model implementable with the apparatus according to the invention in which to the facial texture model is integrated information on the skeletal structure and teeth of the cranial area of the patient. FIG. 5b again shows an example of a facial surface model produceable with the above-described apparatus according to the invention, and FIG. 5c a different projection of the model according to FIG. 5b, which is produced only of information acquirable from the laser line patterns on the patient's face. Comparing FIGS. 5b and 5c illustrates how the facial texture model produceable with the apparatus according to the invention differs from a mere facial surface model.

Figure 6:
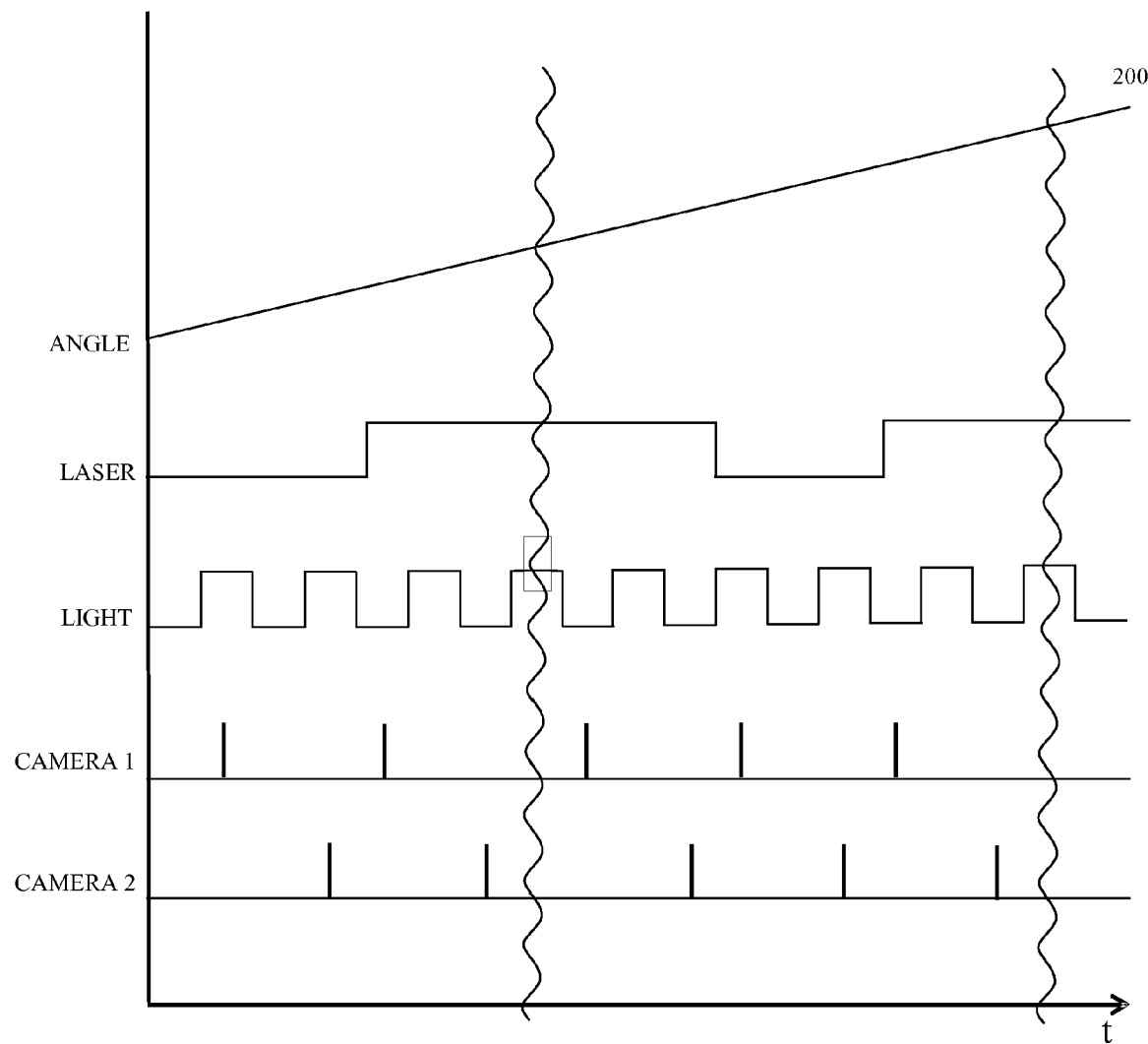
FIG. 6 shows a principle according to one preferable embodiment of the invention for controlling certain operations of the apparatus.

FIG. 6 shows a diagram which illustrates a principle according to which certain operations of the apparatus according to the above-described embodiment can be controlled. In the figure, the imaging of the patient's face is assumed to be implemented—simultaneously with x-ray exposure or as its own imaging—such that the arm part supporting the imaging means (14) is made to rotate such that the receiver module of image information (20) moves from one side of the patient's face to the other for at least 180 degrees, such as for at least 200 degrees, such as for about 260 degrees. During this motion, the patient's face is illuminated by regularly pulsing the light sources (23) of the receiver module of image information (20), whereas the laser light is otherwise kept continuously on but, during the scan, it is momentarily switched off in order to be able to shoot images from the face of the patient positioned at the imaging station (18) also without the laser light pattern. The operations of the apparatus are synchronised to comprise two kinds of periods, during the first of which the laser light is switched off and images are shot of the face during such sequences of the light pulses whereby the patient's face is illuminated, and during the second periods the laser light is again kept on whereby the laser line, when the arm part supporting the imaging means (14) rotates, moves along the patient's face and images are shot of the face during such periods of the light pulses whereby the patient's face is not illuminated. When the imaging employs two colour cameras (22) according to the embodiment of the invention described above, concerning the operation mode shown in FIG. 6, the control as described above is implemented such that the first and the second camera (22) shoot images always during successive light pulses. The image information integrated by the cameras (22) can be read out always during those periods of the light pulsing when image information is not being integrated.

The diagram of FIG. 6 thus shows one principle applicable for use in the invention. However, if desiring to prevent the patient positioned at the imaging station from sensing the flickering of lights caused by the pulsing of facial illumination, the pulse frequency of the illumination must be arranged to be at least 50-60 Hz. Such pulsing would lead, when operating exactly the way shown in FIG. 6, to an unnecessarily large amount of image information for practical implementation of the invention. The above principle can indeed be applied e.g. such that, during the above-described periods, the first and the second camera do not shoot images during each light pulse but only e.g. at times of the order of every tenth pulse, whereby there also is more time for reading the image information from the camera. Thus, in one preferable embodiment of the invention, the means for illuminating the patient's face is controlled to illuminate the patient's face in short pulses, preferably at least at the frequency of 50-60 Hz, the laser or lasers are controlled to produce a laser light pattern on the patient's face otherwise continuously but such that there are periods during the rotation of the arm part, such as less than 10 periods, during which no laser light pattern is produced, and the colour camera or cameras are controlled to shoot images at the first pulse steps when the laser light pattern is directed on the face and when the means for illuminating the patient's face do not illuminate the face, and at the second pulse steps whereby no laser light pattern is directed on the face and when the means for illuminating the patient's face do illuminate the face. One practical way to implement sequencing of shooting images according to the practical mode of operation described above comprises implementing the first and the last period during movement of the imaging means as periods during which the face is imaged without a laser line and for the duration of the movement in question, this kind of periods are arranged for the total of five at even intervals. According to such an embodiment of the invention, for the total of ten colour images of the patient's face would thus be shot from different directions without the laser light pattern, and the angular velocity of the motion of the imaging means from one side of the patient's face to the other can be arranged such that during the four periods falling between these periods, images of the order of 300 are shot of the laser light line directed on the face. It is still evident to those skilled in the art that it is e.g. not necessary to shoot images of the laser light pattern at even intervals and that their number, and the positions from which images of the laser line are shot, may be varied e.g. according to the desired horizontal resolution of the surface construction. It is also not necessary to shoot photographs without the laser line at even intervals and their number and position can be varied according to any particular need as well so that suitable joining points and adequate coverage are achieved for creating a three-dimensional texture model from the partial facial images shot from different directions.

The apparatus according to the invention and its operation mode selection switch (19) can be arranged to enable x-ray imaging and imaging of the patient's face to occur either separately or, in one preferable embodiment of the invention, to be implemented in connection with the same imaging event, even simultaneously. Photographing the face from different directions simultaneously with the x-ray imaging eliminates a need for a separate imaging whereby, among other things, there is no need to calibrate some other imaging device and to position the patient to this other device for a separate facial imaging. Thus, trouble and time are saved when the facial imaging can be performed simultaneously with the x-ray imaging. Also, if one wishes to integrate image information acquired in different ways of imaging, e.g. to be presented in the same three-dimensional model, the combining is then easier as the imaged anatomy has been in the same position and in the set of coordinates according to the same imaging device when imaged. The apparatus enables the use of the laser line to enhance bringing out the facial shapes in more detail by transferring the location of the laser line on the face, by shooting profiles produced by the laser line on the facial surface and by calculating the shape of the facial surface from these profiles.

Above, the invention has been described predominantly with reference to the enclosed figures, but all of the above-described details of the embodiments of the invention are not necessary or the only ones possible considering implementing the invention. The number of colour cameras used in the apparatus can be some other than two and, if the apparatus enables changing the camera location with respect to the imaging station, it is possible to shoot images of the patient's face from different directions even with one camera. In a preferable embodiment of the invention, the apparatus is arranged with a lighting arrangement emitting white light to illuminate the patient's face, which is advantageous considering imaging the facial hues, but it is possible to consider the invention being also utilisable without one or several sources of white light integrated in the apparatus and also with lights of other colours. Furthermore, adequate information for producing a three-dimensional facial texture model can be acquired only from photographing the face from different directions, but the preferable embodiments of the invention also utilise e.g. information on the shapes of the facial soft-tissue surface acquired from an x-ray imaging, or information on the facial surface shapes available from a laser scan of the face.

The receiver module of image information applicable for use in the apparatus can according to the embodiment of above comprise the receiver of x-ray image information (21) arranged substantially in the middle of the module, seen from the horizontal direction, and two lasers (24), and arranged substantially at opposite ends of the module (20) on the one hand a first and a second colour camera (22), on the other hand a first and a second lighting structure (23). When viewing the module (20) in the vertical direction, it may comprise an arrangement in which said lasers (24) are arranged substantially at the edges of the receiver module of image information (20), and said lighting structures (23) to direct light at the imaging station (18) from above and from below said colour cameras (22). The functionality according to the invention for modelling at least part of the face can nevertheless be considered to be achieved with other kinds of arrangements as well, such as with an arrangement which uses two light lines and only one camera.

The colour camera pertaining to the apparatus according to the invention can also be used for other purposes than those described above. The camera or cameras can be arranged to operate as a video camera, whereby it is possible to e.g. monitor and/or save the patient's expressions and possible movements before the x-ray imaging and/or during exposure, with suitable arrangements also in 3D. In the above embodiments, the colour camera or cameras are located to the arm part supporting the imaging means to the substantial proximity of the x-ray detector, but the colour camera or cameras can also be arranged e.g. to the substantial proximity of the x-ray source. Generally, it is advantageous to position the colour camera or cameras, as well as the laser or lasers possibly pertaining to the apparatus, to such structure of the apparatus which is already arranged movable with respect to the imaging station for the purposes of x-ray imaging by the apparatus.

The computer pertaining to the apparatus does not have to be a physically separate device from the imaging means but it can also be integrated as part of the actual imaging device.

The x-ray imaging means of the apparatus preferably enable computed tomography imaging, especially cone-beam computed tomography imaging known to be used in the dental field, the paths of the arm part supporting the x-ray imaging means used in which apparatus are typically arranged to enable rotation of the arm part with respect to a stationary, virtual vertical axis going through the imaging station, which motion is also directly utilisable for producing image information for creating a three-dimensional facial texture model. This property of the imaging apparatus makes implementation of especially the facial laser scanning quite simple, as the x-ray imaging apparatus already includes means to implement movements applicable for use in laser scanning. The laser scanning can in many cases significantly facilitate detection of three-dimensional surface shapes of the patient's face as compared to using information acquired solely from colour photography of the face. In a preferable embodiment of the invention, there is then e.g. an arrangement in which said receiver means of x-ray image information (21) comprise a detector, the dimensions of the area receiving image information of which are at least of the order of centimeters, said structure supporting the imaging means (14) being arranged to be rotatable with respect to a vertical, virtual rotation axis going through a stationary imaging station (18) such that the x-ray source (15) and the receiver means of x-ray image information (21) move on opposite sides of the imaging station (18), in which the control system of the apparatus comprises a control routine, which on the one hand controls the rotating motion of the structure supporting said imaging means (14), the x-ray source (15) and the receiver means of x-ray image information (21) to produce image information, of which with said means for processing information (30) detected by the receiver of x-ray image information (21) can be reconstructed a three-dimensional x-ray image, and on the other hand, controls at least said colour camera (22) to shoot colour images of the face of a patient positioned at the imaging station (18) during said rotating motion, and in which the image information processing means (30) functionally pertaining to the apparatus are arranged to create a three-dimensional model presentable on the display (31) of the patient positioned at the imaging station (18), which model shows at least a portion of the skeletal construction and/or teeth of the patient's cranial area and at least a portion of the texture of the patient's facial area.

According to one preferable embodiment of the invention, the apparatus includes a means for realizing the imaging such that the computed tomography imaging is implemented with a rotation angle of About 200 degrees and the photography with a rotation angle of about 260 degrees. In practice, this can be then implemented such that one manoeuvre of 260 degrees is made, during which the x-ray imaging is started after a movement of 30 degrees and correspondingly stopped earlier than the photography, or by first picking up x-ray image information during a manoeuvre of about 200 degrees in a first direction, continuing the movement in this first direction to the starting position of photography, and implementing photography during a manoeuvre of 260 degrees occurring in the opposite direction. An advantage of the latter alternative is that the motion during mere photography can be implemented as fast (i.e. with higher angular velocity than the x-ray imaging) without the velocity needed in computed tomography imaging limiting the angular velocity, which decreases the risk of the patient's expression changing or of other motions during exposure.

The invention claimed is:
1. A dental imaging apparatus, which apparatus includes
   a support construction (11, 13) for supporting a structure supporting imaging means (14),
   at least one imaging station (18) for placing a patient to the apparatus for imaging,
   in which apparatus the imaging means includes at least an x-ray source (15) and a means for receiving x-ray image information (21), which have been arranged in the apparatus in such a way with respect to said imaging station (18) that the x-ray source (15) and the means for receiving x-ray image information (21) can be positioned at opposite sides of the imaging station (18) such that a beam generated by the x-ray source (15) can be aligned to go through said imaging station (18) and towards said means for receiving x-ray image information (21),
   a control system for controlling operations of the imaging apparatus and
   a means integrated with the imaging apparatus or arranged into functional connection with it for processing information detected at the receiver of x-ray image information (21), characterized in that
   the apparatus includes at least one lighting structure (23) to illuminate the patient's face positioned at the imaging station (18) and said control system includes a means for controlling said lighting structure (23) to produce pulsed white light and/or to produce light of different colours, the apparatus further including a means for photographing (22) a patient's face and/or for producing a moving picture of the patient's face from at least two directions while the patient is positioned at said imaging station (18), said means for photographing forming a module with said means for receiving x-ray image information (21) which means comprises at least one colour camera (22) the location of which with respect to said imaging station is arranged changeable and/or at least two colour cameras being arranged to image the patient's face positioned at the patient support station (18) from different directions, and a means arranged into functional connection with said at least one colour camera (22) for
   processing the image information acquired when imaging the patient's face to create a virtual three-dimensional texture model of the patient's face, and/or for
   combining the image information detected by said at least one colour camera (22), or the three-dimensional texture model created from it, to a surface model of the patient's face to create a virtual three-dimensional texture model of the patient's face.

2. The imaging apparatus according to claim 1, characterized in that the apparatus includes a means for creating a virtual model which comprises x-ray image information at least from a portion of the bones and/or teeth of the patients cranial area integrated with said virtual three-dimensional texture model produced of the patients face.

3. The imaging apparatus according to claim 1, characterized in that the control system of the apparatus comprises a means for implementing the x-ray imaging and the imaging of the patients face at the same time and/or as a combined imaging taking place during one imaging event, and/or the control system of the apparatus comprises a selection means for implementing the x-ray imaging and the imaging of the patient's face either with at least one of the above ways or for implementing at least one of said imagings as a separate imaging.

4. The imaging apparatus according to claim 1, characterized in that said at least one lighting structure (23) and/or at least one colour camera (22) is arranged to the apparatus such that the patients face can be illuminated and imaged from different directions when the patient is positioned at said imaging station (18) arranged for x-ray imaging.

5. The imaging apparatus according to claim 1, characterized in that said means for illuminating the patients face (23) are arranged to comprise a lighting structure which directs light towards the patient's face arranged at the imaging station (18) substantially from above or from below said at least one colour camera (22).

6. The imaging apparatus according to claim 1, characterized in that said means for illuminating the patient's face (23) is arranged to the substantial proximity of said receiver of x-ray image information (21) as a component of the module.

7. The imaging apparatus according to claim 1, characterized in that the apparatus includes at least two colour cameras (22) and they are arranged to be located horizontally at a distance from each other.

8. The imaging apparatus according to claim 1, characterized in that the apparatus includes at least two colour cameras (22) into connection with which is arranged a lighting structure (23) which directs light towards the face of the patient positioned at the imaging station (18) substantially from above and from below of at least two colour cameras (22), which at least two colour cameras (22) and the lighting structures (23) arranged into connection with them are arranged horizontally at a distance from each other on the opposite sides of said receiver of x-ray image information (21).

9. The imaging apparatus according to claim 1, characterized in that said means for illuminating the patient's face (23) and at least one colour camera (22) are arranged into connection with said structure supporting the imaging means (14).

10. The imaging apparatus according to claim 9, characterized in that said structure supporting the imaging means (14) is arranged rotatable with respect to a vertical virtual axis going through the patient support station or some other virtual vertical axis.

11. The imaging apparatus according to claim 1, characterized in that structures, components and control means of the apparatus related to x-ray imaging are arranged to enable dental panoramic imaging, dental computed tomography imaging and/or dental cone-beam computed tomography imaging.

12. The imaging apparatus according to claim 1, characterized in that said structure supporting the imaging means (14) is arranged rotatable with respect to the imaging station (18) for at least 180 degrees and the control system of the apparatus to control said at least one colour camera (22) to shoot at least two colour images of the patients face positioned at the imaging station (18) within the angle range in question.

13. The imaging apparatus according to claim 1, characterized in that information detected by said receiver of x-ray image information (21) and at least one colour camera (22) is arranged to be directed to the same one frame grabber, and/or via the same one Ethernet cable from the imaging device to physically separate means for processing image information (30).

14. The imaging apparatus according to claim 1, characterized in that the apparatus includes a means integrated in it or brought to functional connection with it for creating a three-dimensional surface model of the patients face.

15. The imaging apparatus according to claim 1, characterized in that to the apparatus is arranged at least one laser (24) or other lighting arrangement which is arranged to direct a light pattern on the patients face positioned at the imaging station (18).

16. The imaging apparatus according to claim 14, characterized in that said means for creating the surface model of the patients face includes at least one laser or other light source (24) casting a narrow vertical light pattern on the patients face positioned at the imaging station (18), which light source is placed to said structure supporting the imaging means (14), and that the structure supporting the imaging means (14) in question and said imaging station (18) are arranged movable with respect to each other such that said light pattern can be directed substantially extensively at different locations within the patient's facial area.

17. The imaging apparatus according to claim 14, characterized in that the apparatus includes two lasers (24) or corresponding light sources producing a light pattern arranged substantially on the same vertical virtual axis, which are arranged to the apparatus with respect to the imaging station (18) such that the upper of them illuminates the patients face at least slightly obliquely from above and the lower at least slightly obliquely from below.

18. The imaging apparatus according to claim 14, characterized in that to said structure supporting the imaging means (14) is arranged a receiver module of image information (20) to which is placed each of the receiver of x-ray image information (21), at least one colour camera (22), the means for illuminating the face (23) and the means for producing a laser light pattern (24).

19. The imaging apparatus according to claim 14, characterized in that said structure supporting the imaging means (14) is arranged rotatable with respect to the imaging station (18), said light pattern to move according to the motion of said structure supporting the imaging means (14) and the control system of the apparatus to shoot tens or hundreds of images of the light pattern with said at least one colour camera (22) from different directions within the area of motion area of the structure supporting the imaging means (14) in question.

20. The imaging apparatus according to claim 18, characterized in that seen in the horizontal direction, to the receiver module of image information (20), substantially in the middle of it, is arranged the receiver of x-ray image information (21) and two lasers or corresponding means (24), and substantially at opposite ends of the module (20) are arranged on the one hand the first and the second colour camera (22), on the other hand the first and the second lighting structure (23), and that seen in the vertical direction, said lasers or corresponding means (24) are arranged to the receiver module of image information (20) in question substantially at its edges, and said lighting structures (23) to direct light at the imaging station (18) from above and from below said colour cameras (22).

21. The imaging apparatus according to claim 14, characterized in that the control system of the apparatus comprises a control routine, controlled by which
    the structure supporting the imaging means (14) rotates with respect to the imaging station (18), during which rotation,
    the means for illuminating the patients face (23) are controlled to illuminate the patient's face positioned at the imaging station (18) in short pulses, preferably at least at the frequency of 50 Hz,
    the laser, lasers or corresponding means (24) are controlled to produce a light pattern on the patients face otherwise continuously but such that during the rotation of the structure supporting the imaging means (14), there are moments when the light pattern is not produced, and
    the colour camera or cameras (22) are controlled to shoot images during first steps when the light pattern is directed on the face and when the means for illuminating the patients face (23) do not illuminate the face, and on the other hand during second steps when no light pattern is directed on the face and when the means for illuminating the patients face (23) illuminate the face.

22. The imaging apparatus according to claim 21, characterized in that said structure supporting the imaging means (14) is arranged to rotate with respect to the imaging station (18) for at least 180 degrees and that according to said control routine, there are short periods during the rotation in question, such as less than 10 periods, during which no light pattern is directed on the patient's face and during which the colour camera or cameras (22) are controlled to shoot images at phases when the means for illuminating the patients face do produce a light pulse.

23. The imaging apparatus according to claim 1, characterized in that said receiver means of x-ray image information (21) comprise a detector, the dimensions of the area receiving image information of which are at least of the order of centimeters, said structure supporting the imaging means (14) is arranged to be rotatable with respect to a vertical, virtual rotation axis going through the stationary imaging station (18) such that the x-ray source (15) and the receiver means of x-ray image information (21) move on opposite sides of the imaging station (18), in which the control system of the apparatus comprises the control routine, which on the one hand controls the rotating motion of the structure supporting said imaging means (14), the x-ray source (51) and the receiver means of x-ray image information (21) to produce image information, of which with said means for processing information (30) detected by the receiver of x-ray image information (21) can reconstruct a three-dimensional x-ray image, and on the other hand, controls at least said colour camera (22) to shoot colour images of the patients face positioned at the imaging station (18) during said rotating motion, and that the image information processing means (30) functionally pertaining to the apparatus are arranged to create a three-dimensional model of the patient positioned at the imaging station (18) which is presentable on a display (31), which model shows at least a portion of the bones and/or teeth of the patient's cranial area and at least a portion of the texture of the patient's facial area.

24. An apparatus according to claim 1, characterized in that the apparatus includes a means for producing a green laser or other light fan and directing it towards the patients face positioned at the imaging station to create a substantially vertical narrow line of light on the face.

25. An apparatus according to claim 1, characterized in that the apparatus includes two lasers (24), the first of which is arranged to produce laser light of a first colour and the second of a second colour.

26. An apparatus according to claim 1, characterized in that the apparatus includes at least two light sources (23) in front of which is arranged a diffusing foil and/or a polarizer.

* * * * *